US012735747B2

(12) United States Patent
Zisapel et al.

(10) Patent No.: US 12,735,747 B2
(45) **Date of Patent: *Sep. 15, 2026**

(54) METHOD FOR DIAGNOSING AND TREATING SUBJECTS HAVING SINGLE NUCLEOTIDE POLYMORPHISMS IN CHROMOSOME 2, 2:107,510,000-107,540,000 LOCUS

(71) Applicant: NEURIM PHARMACEUTICALS (1991) LTD., Tel Aviv (IL)

(72) Inventors: Nava Zisapel, Tel Aviv (IL); Moshe Laudon, Tel Aviv (IL)

(73) Assignee: NEURIM PHARMACEUTICALS (1991) LTD., Tel Aviv (IL)

( * ) Notice: Subject to any disclaimer, the term of this patent is extended or adjusted under 35 U.S.C. 154(b) by 427 days.

This patent is subject to a terminal disclaimer.

(21) Appl. No.: 18/475,641

(22) Filed: Sep. 27, 2023

(65) Prior Publication Data

US 2024/0068035 A1 Feb. 29, 2024

Related U.S. Application Data

(63) Continuation-in-part of application No. 17/815,806, filed on Jul. 28, 2022, now Pat. No. 11,807,907, which is a continuation-in-part of application No. PCT/IB2022/054347, filed on May 10, 2022.

(60) Provisional application No. 63/187,078, filed on May 11, 2021.

(51) Int. Cl.

| | |
|---|---|
| ***C12Q 1/68*** | (2018.01) |
| ***A61K 31/4045*** | (2006.01) |
| ***A61P 25/28*** | (2006.01) |
| ***C12Q 1/6883*** | (2018.01) |

(52) U.S. Cl.

CPC ........ *C12Q 1/6883* (2013.01); *A61K 31/4045* (2013.01); *A61P 25/28* (2018.01); *C12Q 2600/106* (2013.01); *C12Q 2600/156* (2013.01); *C12Q 2600/158* (2013.01)

(58) Field of Classification Search

None

See application file for complete search history.

(56) References Cited

U.S. PATENT DOCUMENTS

| | | | |
|---|---|---|---|
| 2013/0324583 | A1 | 12/2013 | Laudon et al. |
| 2014/0377351 | A1 | 12/2014 | Zisapel et al. |
| 2015/0141491 | A1 | 5/2015 | Nagy |

FOREIGN PATENT DOCUMENTS

| | | | |
|---|---|---|---|
| WO | 2008/008553 | A2 | 1/2008 |
| WO | 2009/007934 | A2 | 1/2009 |

OTHER PUBLICATIONS

Office Action dated Dec. 30, 2025 issued in Taiwanese Patent Application No. 111117602 with Translation. (21 pages).

Bhute et al., "Molecular Pathogenesis and Interventional Strategies for Alzheimer's Disease: Promises and Pitfalls." ACS Pharmacology & Translational Science. vol. 3, Issue 3, 2020, pp. 472-488.

Cummings et al., "Treatment Combinations for Alzheimer's Disease: Current and Future Pharmacotherapy Options." Journal of Alzheimer's Disease. vol. 67, Issue 3, 2019, pp. 779-794.

Sumiyoshi, T., et al.,: "Serotonin1A receptors in the pathophysiology of schizophrenia: development of novel cognition-enhancing therapeutics", Advances in Therapy, vol. 25, No. 10, Oct. 1, 2008, pp. 1037-1056.

Verdurand, M., et al., "Hippocampal 5-HT1Areceptor expression changes in prodromal stages of Alzheimer's disease: Beneficial or deleterious?", Neuropharmacology, vol. 123, Jun. 21, 2017, pp. 446-454.

Schneider, L.S., et al., "A Polymorphism Cluster at the 2q12 locus May Predict Response to Piromelatine in Patients with Mild Alzheimer's Disease", The Journal of Prevention of Alzheimer's Disease, Nov. 21, 2021 , pp. 1-8.

Notification of Transmittal of the International Search Report and the Written Opinion of the International Searching Authority dated Aug. 19, 2022, 16 pages.

Blacker et al., "ApoE-4 and age at onset of Alzheimer's disease: The NIMH Genetics Initiative", Neurology, 48, Jan. 1997, 139-147 pgs.

Amos, "Even small SNP clusters are non-randomly distributed: is this evidence of mutational non-independence?", Proc. R. Soc. B (2010) 277, 1443-1449.

Liu et al., "Apolipoprotein E and Alzheimer disease: risk, mechanisms, and therapy", Nat Rev Neurol. Feb. 2013 ; 9(2): 106-118.

Rapp MD, Ph.D., et al., "Cortical Neuritic Plaques and Hippocampal Neurofibrillary Tangles are Related to Dementia Severity in Elderly Schizophrenia Patients", Schizophr Res. Jan. 2010; 116(1): 90-96.

Vivanti et al., "The prevalence and incidence of early-onset dementia among adults with autism spectrum disorder", Autism Research. 2021;14:2189-2199.

Vivanti et al., "Early-onset dementia in autism spectrum disorder", Neurology, vol. 17, Oct. 2021, p. 595.

Sotos et al.; "The Transitivity Misconception of Pearson's Correlation Coefficient", Statistics Education Research Journal, 8(2), 2009, pp. 33-55.

Andiappan et al., Evaluating the transferability of Hapmap SNPs to a Singapore Chinese population, BMC Genetics. 2010. 11: 36, 16 pages.

(Continued)

*Primary Examiner* — Jehanne S Sitton

(74) *Attorney, Agent, or Firm* — Rothwell, Figg, Ernst & Manbeck, P.C.

(57) ABSTRACT

Methods and products for identifying individuals who are likely to respond in a positive (benefit) or negative (harm) manner to a pharmacological drug treatment intended for treating or preventing a neuropsychiatric disorder, neurodegeneration, sleep-wake cycles such including and not limited to schizophrenia, autism, attention deficit disorders and Alzheimer's disease based on single nucleotide polymorphisms (SNP) chromosome 2, 2:107,510,000-107,540,000 locus (as disclosed in the Genome Reference Consortium Human genome build 37 (GRCh37)).

21 Claims, 6 Drawing Sheets

Specification includes a Sequence Listing.

(56) References Cited

OTHER PUBLICATIONS

Alzheimers (from the Internet: alzheimersnewstoday.com/piromelatine/; pp. 1-2, Feb. 2018).

Dou et al., "Comparative safety and effectiveness of cholinesterase inhibitors and memantine for Alzheimer's disease: a network meta-analysis of 41 randomized controlled trials", Alzheimer's Research & Therapy, 2018; 10:126, pp. 1-10.

Non-Final Office Action issued in U.S. Appl. No. 17/740,670 dated Nov. 10, 2022, 25 pages.

rs12328439 2:107516926 (2:107516902-107516950)

WT: TTCTTGCTCCCCACTAGGTCACAATGTCCTAGCATCATCAACCCTAACA (SEQ ID NO: 1)

SNP: TTCTTGCTCCCCACTAGGTCACAACGTCCTAGCATCATCAACCCTAACA (SEQ ID NO: 2)

rs62155556 2:107521253 (2:107521229-107521277)

WT: CCATTCCCCTTTGAGCCTGGAGATTTTAATTGAATAAAAATTACAAATT (SEQ ID NO: 3)

SNP: CCATTCCCCTTTGAGCCTGGAGATATTAATTGAATAAAAATTACAAATT (SEQ ID NO: 4)

rs62155557 2:107522069 (2:107522045-107522093)

WT: ACGCTTTTTTGAAATAATGAGAGCGCACTTCAACAGAGAAGGCTTTGGA (SEQ ID NO: 5)

SNP: ACGCTTTTTTGAAATAATGAGAGCTCACTTCAACAGAGAAGGCTTTGGA (SEQ ID NO: 6)

rs62155558 2:107523546 (2:107523522-107523570)

WT: CCTTCCTGAGCCACTGAAGGTTGTGGGGAAAATAATTTAACACTTCAGT (SEQ ID NO: 7)

SNP: CCTTCCTGAGCCACTGAAGGTTGTAGGGAAAATAATTTAACACTTCAGT (SEQ ID NO: 8)

rs17033479 2:107525598 (2:107525574-107525622)

WT: CTGGGTTGCCCAGGGAGCTTGTCTATACCAGAGTGGCTAAAATTATGTC (SEQ ID NO: 9)

SNP: CTGGGTTGCCCAGGGAGCTTGTCTGTACCAGAGTGGCTAAAATTATGTC (SEQ ID NO: 10)

rs9789618 2:107535946 (2:107535922-107535970)

WT: AAATGAGGACACTGGATGATATTGTTAACCTTTGGTGATGCTAACTAAA (SEQ ID NO: 11)

SNP: AAATGAGGACACTGGATGATATTGTTAACCTTTGGTGATGCTAACTAAA (SEQ ID NO: 12)

FIG. 3

METHOD FOR DIAGNOSING AND TREATING SUBJECTS HAVING SINGLE NUCLEOTIDE POLYMORPHISMS IN CHROMOSOME 2, 2:107,510,000-107,540,000 LOCUS

CROSS-REFERENCE TO RELATED APPLICATIONS

This application is a continuation-in-part of U.S. application Ser. No. 17/815,806, filed Jul. 28, 2022, which is a continuation-in-part of PCT/IB2022/054347, filed May 10, 2022, which claims priority benefit of U.S. provisional application No. 63/187,078 filed May 11, 2021, the entire contents of which are incorporated herein by reference.

REFERENCE TO SEQUENCE LISTING

The present application includes a Sequence Listing filed in electronic format. The "Sequence Listing" submitted electronically concurrently herewith in computer readable form (CRF) is entitled "2007-145 ST26.XML," was created on Jul. 28, 2022, and is 12,288 bytes in size. The information in the electronic format of the Sequence Listing is part of the present application and is incorporated herein by reference in its entirety.

FIELD OF THE DISCLOSURE

This disclosure relates to methods for treating subjects, including improving mental performance and intellectual ability in patients with mental disorders, based on benefit or harm from administration of certain drug products to the subject based on single nucleotide polymorphisms in chromosome 2, 2:107,510,000-107,540,000 locus (as disclosed in the Genome Reference Consortium Human genome build 37 (GRCh37)) referred to as 2:107,510,000-107,540,000 locus.

BACKGROUND

Declining memory, mental performance, and intellectual ability in patients with neurological and neurodegenerative diseases are notoriously difficult to understand and treat. Patients respond differently to treatments based on mysterious and unknown reasons. Hence, the symptoms and signs of patients suffering from such diseases remain poorly addressed by medicine.

Worldwide, it is estimated that about 50 million people have dementia and, every year, there are nearly 10 million new cases. Alzheimer's disease (associated with amyloid β-protein (Aβ) pathology) accounts for 60% to 70% of these patients (who.int/news-room/fact-sheets/detail/dementia—dated Sep. 21, 2020).

Schizophrenia is a chronic mental disease that disturbs several cognitive functions, such as memory, thought, perception and volition. Major symptoms include hallucinations (typically hearing voices), delusions, and disorganized thinking. Other symptoms include social withdrawal, decreased emotional expression, and apathy. It affects approximately 0.5%-1% of the worldwide population. In 2017, there were an estimated 1.1 million new cases and in 2019 a total of 20 million cases globally. Individuals aged 55 years and older will soon account for 25% or more of the total population of patients with schizophrenia worldwide. The prevalence of schizophrenia in older adults set to double and reach 1.1 million people in the US by 2025. Older patients with schizophrenia include individuals with an early onset that persists into later life and those with a late onset of this condition. Individuals with schizophrenia are characterized by a diverse set of motor symptoms, among them involuntary, uncoordinated, and inhibited movement. (Abboud et al. Eur Psychiatry. 2017, 44:125-133). Older adults with schizophrenia have significant cognitive deficits in executive functioning, speed of processing, attention/vigilance, working memory, verbal learning, visual learning, reasoning, and problem-solving (Daban C, et al. J Psychiatr Res. 2005; 39: 391-8, Schäppi L, et al. Front Psychiatry. 2018; 9:129). Differentiating between schizophrenia and Alzheimer disease with psychosis in older adults can be difficult (Radhakrishnan et al Advances in psychiatric treatment 2012, 18:144-153), It is interesting to note that older adults with schizophrenia and a high anticholinergic burden have a cognitive impairment profile consistent with that observed in Alzheimer dementia. Therefore, symptomatic patients who are diagnosed with symptomatic Alzheimer's disease may in fact have dementia related to schizophrenia.

Autism or autism spectrum disorder (ASD) is a complex neurodevelopmental condition characterized by persistent difficulties in social interactions and communication, as well as restricted interests and repetitive behaviors. ASD is typically diagnosed during the first three years of life and manifests in characteristic symptoms or behavioral traits (core symptoms). A diagnosis of ASD now includes several conditions that used to be diagnosed separately: autistic disorder, pervasive developmental disorder not otherwise specified (PDD-NOS), and Asperger syndrome. All of these conditions are now encompassed by the diagnostic criteria for autism spectrum disorder as set forth in the American Psychiatric Association's Diagnostic & Statistical Manual of Mental Disorders, Fifth Edition (DSM-V). In addition to the spectrum of symptoms seen within these principal diagnostic criteria, individuals with autism may also experience co-occurring conditions such as depression, anxiety, insomnia or behavioral disorders (e.g. irritability, hyperactivity, aggression), intellectual disability, epilepsy, as well as non-neurological comorbidities, including blood hyperserotonemia, immune dysregulation, and GI dysfunction (e.g., chronic constipation, diarrhea, abdominal pain, and gastroesophageal reflux). The prevalence of early onset dementia (at age<65 years) is considerably higher among people with diagnosis of ASD (4.04%) and people with ASD and intellectual disability (5.22%) than among the healthy population (0.97%) (Vivanti et al. Autism Res. 2021; 14(10):2189-2199.) Autism and schizophrenia can have overlapping symptoms, and both may involve genetics and certain areas of the brain (Pina-Camacho et al BJPsych Advances 2016; 22: 316-324). Therefore, some demented patients may in fact have dementia related to ASD or schizophrenia.

Serotonin (5-HT) receptors have been suggested to play key roles in psychosis, cognition, and mood via influence on neurotransmitters, synaptic integrity, and neural plasticity. Specifically, genetic evidence indicates that 5-HT1A, 5-HT2A, and 5-HT2C receptor single-nucleotide polymorphisms (SNPs) are related to psychotic symptoms, cognitive disturbances, and treatment response in schizophrenia (Sumiyoshi et al Adv Ther. 2008; 25(10):1037-1056.).

Rare copy number variants (deletions or duplications; CNVs) in Chromosome 2 region 2q12.2 (2: 106992995-108507424 in GRCh37) in the vicinity of or encompassing the 2:107,510,000-107,540,000 locus were reported in three of 1656 (0.18%) people with schizophrenia and in one of 4036 (0.02%) healthy controls (Magri et al PLos ONE 2010; 5 (10): e13422, Kirov et al. Hum Mol Genet 2009; 18:

1497-1503., Need et al. PLoS Genet 2009; 5: e1000373, Grozeva et al Arch Gen Psychiatry 2010; 67(4):318-327) and suggested as a schizophrenia susceptibility risk factor, but not formally associated with the disease nor with symptomatic Alzheimer's disease. None of the genes in the deleted segments were implicated in schizophrenia. None of these publications disclosed the high proximity SNPs of the present invention and their high frequency (ca. 25%) among patients diagnosed with symptomatic Alzheimer's disease.

Melatonin receptor agonists (e.g., melatonin, ramelteon, agomelatine, piromelatine) were considered for the treatment and prevention of neurodegenerative disorders including schizophrenia, autism spectrum disorder (ASD), Alzheimer's disease, ischemic stroke and depression, (Srinivasan et al. Int J Alzheimer's Dis 2010; 2011:741974, Wade et al Clin Interv Aging. 2014; 9:947-61, Altinyazar and Kiylioglu Ther Adv Psychopharmacol. 2016; 6(4): 263-268, U.S. Pat. No. 8,242,163B2, Cho et al., Brain Research 755:335-338, 1997; Reiter et al., Exp. Biol. Med. 230:104-17, 2005, Norman and Olver Expert Opinion on Pharmacotherapy 2019, 20: 647-656, Morera-Fumero and Abreu-Gonzalez Int. J. Mol. Sci. 2013, 14, 9037-9050, Gagnon and Godbout Current Developmental Disorders Reports 2018; 5:197-206). However, none of these were unequivocally shown to be effective in such studies.

5-HT1 receptor agonists have been considered for cognitive enhancement in schizophrenia (Sumiyoshi et al Adv Ther. 2008; 25(10):1037-1056.), autism (Dunn et al. Int J Neuropsychopharmacol. 2020; 23(8):533-542), Alzheimer's disease (Verdurand and Zimmer, Neuropharmacology 2017; 123:446-454), depression anxiety and psychotic disorders (Celada et al CNS Drugs (2013; 27:703-716). However, the pharmaceutical industry has repeatedly failed in developing an effective treatment for Alzheimer's disease, autism and schizophrenia, with a string of product failures in recent years including pimavanserin, bitopertin, luvadaxistat, crenezumab, troriluzole, solanezumab, gantenerumab, semagacestat, avagacestat, verubecestat, atabecestat, and lanabecestat.

Therefore, there is a long-felt and unmet need to provide products for treating dementia, mental performance, and intellectual disability in subjects with neurological and neurodegenerative diseases including schizophrenia, attention deficit disorders, ASDs, Alzheimer's disease and associated symptoms. Identification of subpopulations with different etiologies among patients diagnosed with dementia may lead to a more efficient drug development based on precision medicine.

SUMMARY OF THE INVENTION

The present invention relates to a method of identifying a distinct subgroup of demented patients with Cognitive Impairment Associated With Schizophrenia (CIAS), or attention deficit disorder, or autism, carrying polymorphism in chromosome 2, 2:107,510,000-107,540,000 locus (as disclosed in the Genome Reference Consortium Human genome build 37 (GRCh37)), (herein referred to as 2:107,510,000-107,540,000 locus) and identifying predictors of response to treatments aimed at treating mental disorders and particularly improving the intellectual ability in the patients, specifically predict whether such patients will be harmed or benefited by administration of certain drugs. The method may also include treating patients according to methods of the present disclosure based on their identified genotypes.

The present disclosure includes methods for identifying a genotype of a human subject afflicted with a neurological or mental disorder or disease and then treating the human subject with a suitable treatment. The present disclosure includes determining if the human subject has a single nucleotide polymorphism (SNP) in chromosome 2, 2:107,510,000-107,540,000 locus and administering a melatonin/5-HT1A receptor agonist to the human subject if the human subject has been diagnosed with schizophrenia, an attention deficit disorder, or an autism spectrum disorder and has a SNP in the 2:107,510,000-107,540,000 locus.

The present disclosure includes methods of treating a patient diagnosed with plausible Cognitive Impairment Associated With Schizophrenia (CIAS), an attention deficit disorder or autism spectrum disorder and having a SNP selected from rs12328439 and/or rs62155556 and/or rs62155557 and/or rs62155558 and/or rs17033479 and/or rs9789618, comprising administering piromelatine to the patient.

The present disclosure includes methods of predicting the response of a subject to a therapy comprising a melatonin/5-HT1A receptor agonist by determining if the subject has a SNP selected from rs12328439 and/or rs62155556 and/or rs62155557 and/or rs62155558 and/or rs17033479 and/or rs9789618, wherein if the patient has been diagnosed with schizophrenia, an attention deficit disorder, an autism spectrum disorder, or a dementia that is not related to Alzheimer's disease, and has a SNP selected from rs12328439 and/or rs62155556 and/or rs62155557 and/or rs62155558 and/or rs17033479 and/or rs9789618 predicts that the subject will respond positively to a therapy comprising the melatonin/5-HT1A receptor agonist.

The present disclosure includes methods of improving attention and focus a subject with an attention disorder associated with schizophrenia, an attention deficit disorder, or an autism spectrum disorder, comprising determining if the subject has a SNP in at least one of rs12328439 and/or rs62155556 and/or rs62155557 and/or rs62155558 and/or rs17033479 and/or rs9789618, and if the patient has the SNP, then administering a melatonin/5HT1A receptor agonist therapy to the subject.

The present disclosure includes methods of identifying a prognostic genotype of a subject's response to a drug for treating mental disorders and/or intellectual ability in a human subject, the method comprising determining the genotype of the subject of at least 1 position of single nucleotide polymorphism (SNP) selected from 2: 107516926 and/or 2:107521253 and/or 2:107522069 and/or 2:107523546 and/or 2: 107525598 and/or 2:107535946, and/or a SNP in linkage disequilibrium with any one of said SNPs, wherein said SNPs are as disclosed in the GRCh37, and wherein the presence of:

at least one C allele at rs12328439 (T>C); and/or
at least one A allele at rs62155556 (T>A); and/or
at least one T allele at rs62155557 (G>T); and/or
at least one A allele at rs62155558 (G>A); and/or
at least one G allele at rs17033479 (A>G); and/or
at least one A allele at rs9789618 (T>A) is indicative of a subject having a positive response to a melatonin/5-HT1A receptor agonist when the subject has been diagnosed with schizophrenia, an attention deficit disorder, or an autism spectrum disorder. Most SNPs in the human genome reside near other SNPs to form small clusters. Even small SNP clusters are non-randomly distributed, which indicates that there is mutational non-independence. The present disclosure provides the six SNPs for use according to the methods of the present disclosure in such a cluster.

The present disclosure includes methods of administering the melatonin/5-HT1A receptor agonist to the subject diagnosed with schizophrenia, an attention deficit disorder, or an autism spectrum disorder.

The present disclosure includes methods of treating a patient with schizophrenia, an attention deficit disorder, or an autism spectrum disorder, comprising determining that the patient carries a SNP in at least one of rs12328439, rs62155556, rs62155557, rs62155558, rs17033479, and rs9789618, and administering a melatonin/5-HT1A receptor agonist to the subject.

In one aspect, the subject has been diagnosed with an Autism Spectrum Disorder, schizophrenia, an attention deficit disorder, or attention deficit and/or hyperactivity disorder.

In one aspect, the subject has an intellectual disability, epilepsy, an anxiety disorder, a mood disorder, a disorder of social interaction, irritability, aggression, self-injurious behavior, hyperactivity, and/or inattention. In one aspect, the subject has Fragile X syndrome.

Other features and characteristics of the subject matter of this disclosure, as well as the methods of operation, functions of related elements of structure and the combination of parts, and economies of manufacture, will become more apparent upon consideration of the following description and the appended claims, all of which form a part of this specification.

BRIEF DESCRIPTION OF THE DRAWINGS

FIG. 3 shows DNA sequences of the wild type and respective SNPs of rs12328439, rs62155556, rs62155557, rs62155558, rs17033479, and rs9789618 (as disclosed in the Genome Reference Consortium Human genome build 37 (GRCh37)).

DETAILED DESCRIPTION

Figure 1:
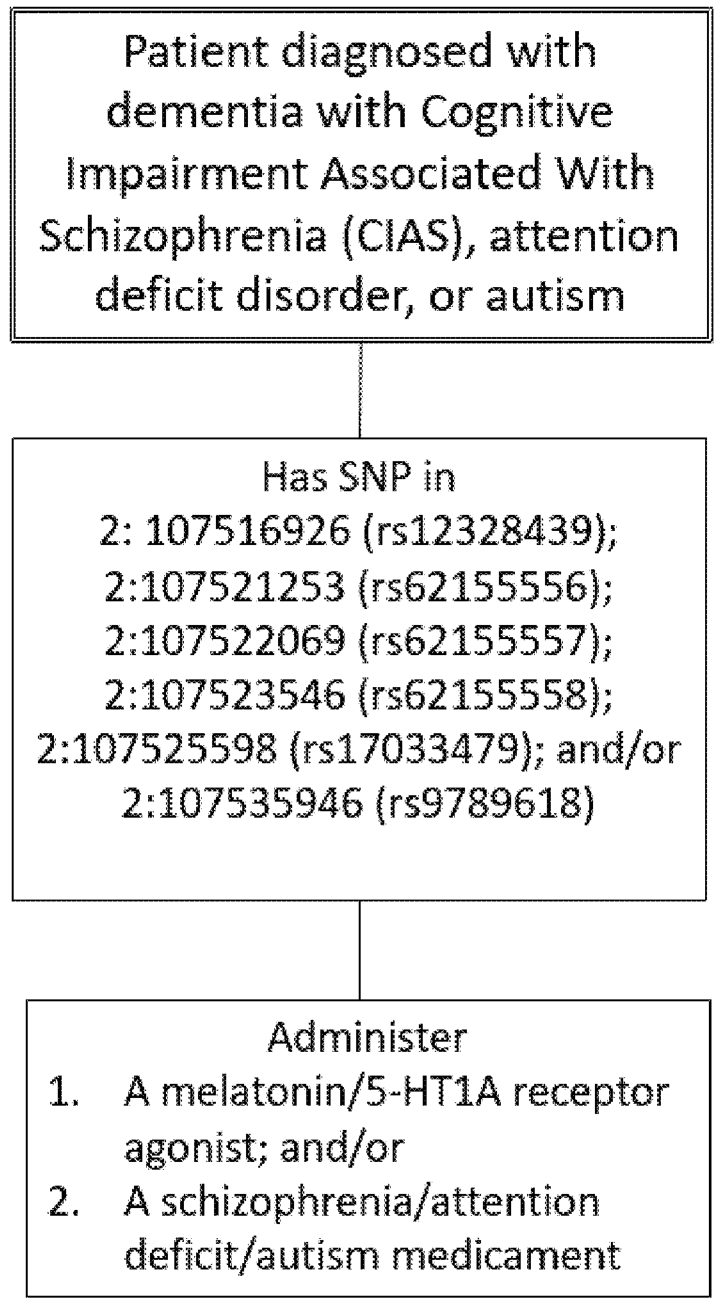
FIG. 1 shows a flowchart of the method of the present disclosure.
Figure 2:
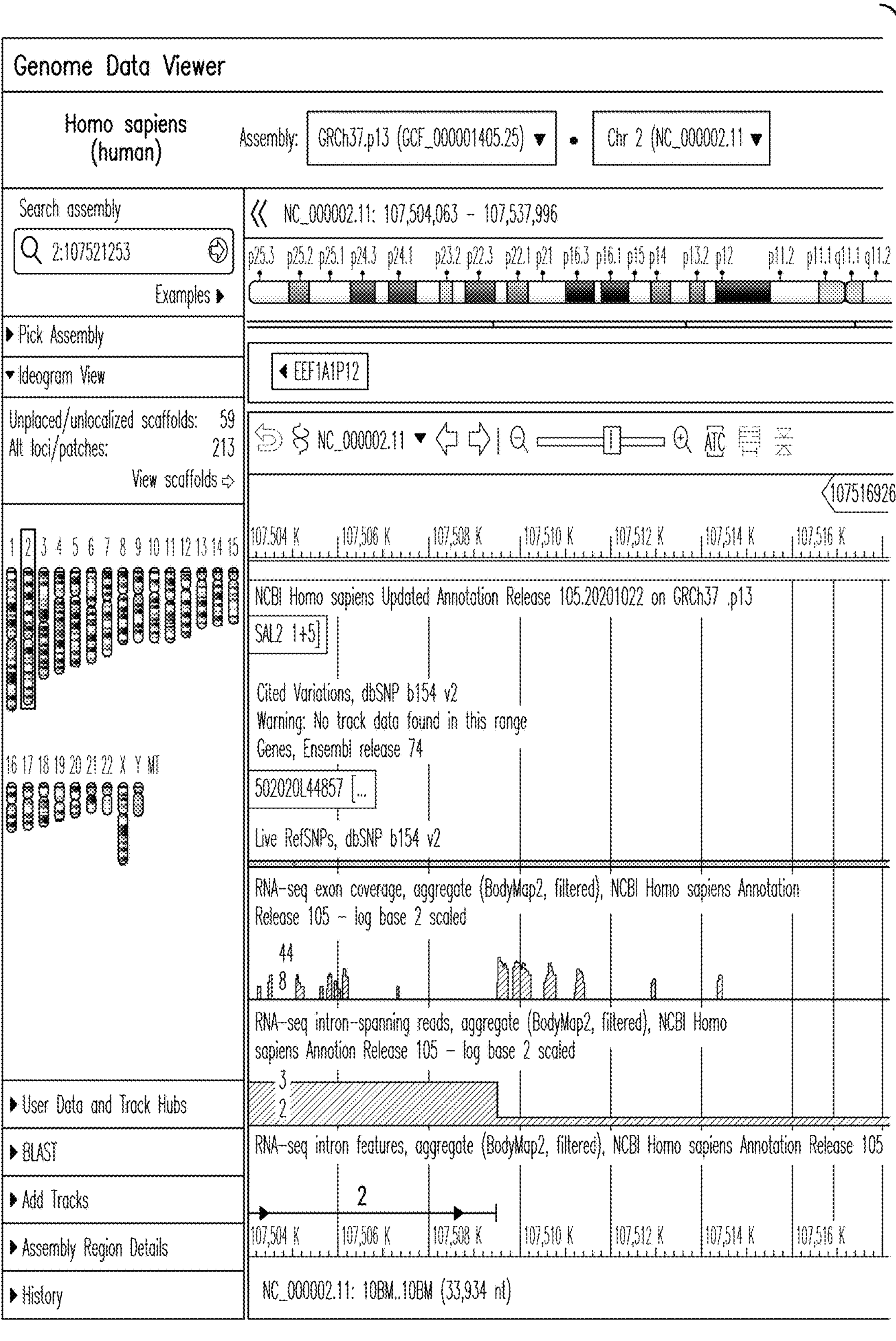
FIG. 2 shows the chromosome 2, 2:107,510,000-107,540,000 locus (as disclosed in the Genome Reference Consortium Human genome build 37 (GRCh37)) (ncbi.nlm.nih.gov/genome/gdv/browser/genome/?id=GCF_000001405.25).
Figure 2:
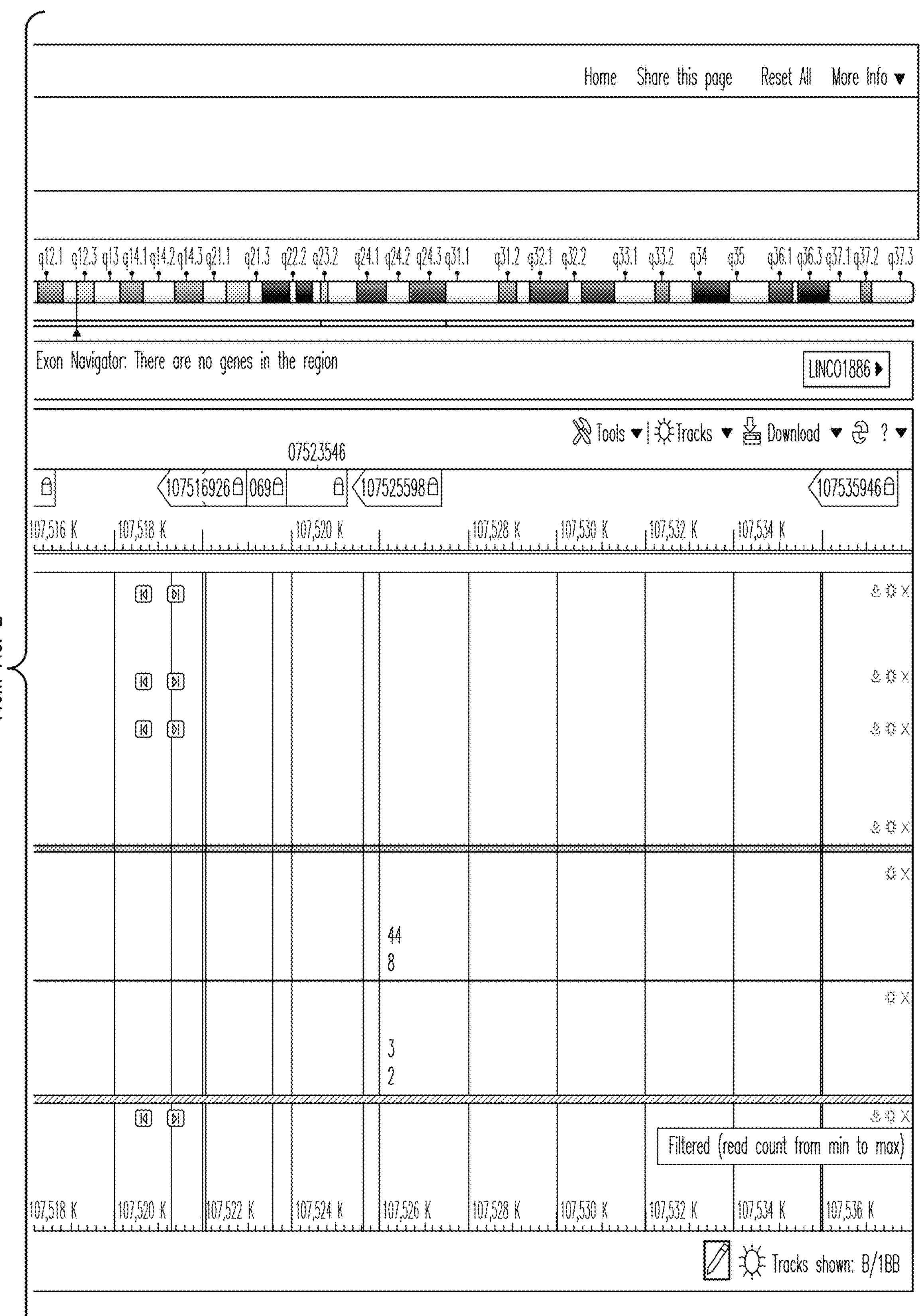

While aspects of the subject matter of the present disclosure may be embodied in a variety of forms, the following description is merely intended to disclose some of these forms as specific examples of the subject matter encompassed by the present disclosure. Accordingly, the subject matter of this disclosure is not intended to be limited to the forms or embodiments so described.

The singular forms "a," "an," and "the" include plural referents unless the context clearly dictates otherwise.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" would find direct support due to this definition.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about ±10% of the numerical value. In another aspect, the degree of flexibility can be within about ±5% of the numerical value. In a further aspect, the degree of flexibility can be within about ±2%, ±1%, or ±0.05%, of the numerical value.

Generally herein, the term "or" includes "and/or."

As used herein, a plurality of compounds, elements, or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Furthermore, certain compositions, elements, excipients, ingredients, disorders, conditions, properties, steps, or the like may be discussed in the context of one specific embodiment or aspect or in a separate paragraph or section of this disclosure. It is understood that this is merely for convenience and brevity, and any such disclosure is equally applicable to and intended to be combined with any other embodiments or aspects found anywhere in the present disclosure and claims, which all form the application and claimed invention at the filing date. For example, a list of method steps, active agents, kits, or compositions described with respect to a therapeutic agent or method of treating a certain subject is intended to and does find direct support for embodiments related to compositions, formulations, therapeutic active agents, and methods described in any other part of this disclosure, even if those method steps, active agents, kits, or compositions are not re-listed in the context or section of that embodiment or aspect.

In a first aspect, the methods of the present disclosure are based on the surprising and paradoxical responses of subjects to melatonin/5-HT1A agonist drugs based on their diagnosed disease/disorder status in combination with their genotype. The inventors have identified six single nucleotide polymorphisms in the 2:107,510,000-107,540,000 locus that are independent predictors of paradoxical (favorable or unfavorable) responses of subjects to melatonin/5-HT1A agonist drug treatment, the favorability (i.e., benefit) or unfavorability (i.e., detriment) of the treatments being dependent on the diagnosed disease/disorder of the subjects. Particularly, the presence of one or more of these SNPs are predictive of favorable responses to the treatment in intellectual ability and neuropsychiatric measures—that may be useful in schizophrenia, an attention deficit disorder, and ASD patients. Thus, the present disclosure provides novel and unexpected methods of using endophenotypic variations in the 2:107,510,000-107,540,000 locus to assess treatment outcome using cognition-enhancing medications.

The phrase "symptomatic Alzheimer's disease" refers to clinical findings of Alzheimer's disease symptoms in a subject.

Suitable melatonin and/or 5-HT1a receptors agonists for use in the present invention include (but are not restricted to) such compounds described in U.S. Pat. Nos. 7,635,710, 8,569,355, 5,151,446; 5,318,994; 5,385,944; 5,403,851; and International Patent Nos. WO2007/093880A2 and WO2007/093880A3, which are incorporated herein by reference in their entireties.

In one non-limiting and exemplary aspect, the invention relates to compounds having the formula (I):

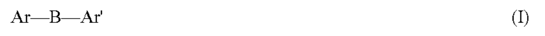
Ar—B—Ar' (I)

wherein:

B represents:

—X—Y—Z—wherein

X represents $-(CH_2)_n-$ (wherein n is 0-6) in which the alkyl moiety is linear or branched, Y represents oxygen, sulphur, >NH or is absent, Z represents >C═O, >O, >COO or is absent, wherein at least one of X, Y and Z must be present;

Ar represents an indole nucleus ring system:

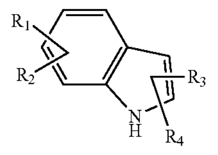

Ar' represents an alpha-, beta- or gamma-pyrone nucleus ring system:

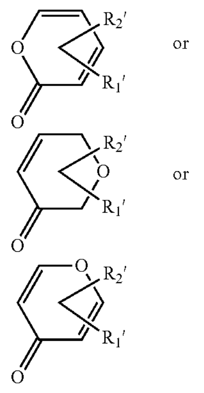
or
or wherein each of $R_{1-4}$ substitutes the ring Ar at any available position (including the N-position) and each of $R_{1'-2'}$ substitutes the ring Ar' at any available position and wherein each of $R_{1-4}$ and $R_{1'-2'}$ independently represents hydrogen, oxygen, halo, halo-$C_{1-5}$ alkyl, aryl, acyl, a $C_{5-7}$ heterocyclic group containing 1-3 hetero atoms independently selected from nitrogen, oxygen and sulphur; a $C_{6-8}$ heteroaryl group containing 1-3 hetero atoms independently selected from nitrogen, oxygen or sulfur; $C_{1-5}$ alkyl, $C_{2-5}$ alkenyl, $C_{2-5}$ alkynyl, aryl-$C_{1-5}$ alkyl, aryl-$C_{2-5}$ alkenyl, aryl-$C_{2-5}$ alkynyl, hydroxy-$C_{1-5}$ alkyl, nitro, amino, cyano, cyanamido, guanidino, amidino, acylamido, $C_{1-5}$ alkylamine, $C_{1-5}$ alkylamido, hydroxy, thiol, acyloxy, azido, $C_{1-5}$ alkoxy, carboxy, carbonylamido or styryl; wherein said arylalkyl, arylalkenyl, aralalkynyl, or styryl group optionally can be ring-substituted by one to four substituents independently selected from the group consisting of hydrogen, halo, halo-$C_{1-5}$ alkyl, aryl, a $C_{5-7}$ heterocyclic group containing 1-3 hetero atoms independently selected from nitrogen, oxygen or sulphur; a heteroaryl group containing 1-3 hetero atoms independently selected from nitrogen, oxygen and sulphur; $C_{1-5}$ alkyl, $C_{2-5}$ alkenyl, $C_{2-5}$ alkynyl, aryl-$C_{1-5}$ alkyl, aryl-$C_{1-5}$ alkenyl, aryl-$C_{2-5}$ alkynyl, hydroxy-$C_{1-5}$ alkyl, nitro, amino, cyano, cyanamido, guanidino, amidino, acylamido, hydroxy, thiol, acyloxy, azido, alkoxy, carboxy, carbonylamido, S-alkyl or alkylthiol;

and either of $R_3$ or $R_4$ further can include or represent a bond to B;

wherein Ar can be bonded to B at any position on the Ar ring not substituted by $R_1$ and $R_2$, including the N-position, and Ar' can be bonded to B at any carbon on the Ar' ring not substituted by $R_{1'}$ or $R_{2'}$;

or a pharmaceutically acceptable salt or stereoisomer thereof.

As used herein, "aryl" represents phenyl or naphthyl.

Without prejudice to the generality of the compounds of the present invention, a subgroup of presently preferred compounds is defined such that in formula (I), X is $-(CH_2)_2-$, Y is >NH or >0, Z is >C=O, Ar is an indole containing a bond, $R_3$, to X at position 3 of the indole ring, $R_1$ is methoxy on position 5 of the indole ring, each of $R_2$ and $R_4$ is hydrogen, and either (a) Ar' is a gamma-pyrone bonded to Z on position 2 of the pyrone ring, $R_{1'}$ is hydrogen or a hydroxy group at position 5 of the pyrone ring, and $R_{2'}$ is hydrogen or a carboxy group at position 6 of the gamma-pyrone ring, or (b) Ar' is an alpha-pyrone ring bonded to Z at position 5 of the pyrone ring, $R_{1'}$ and $R_{2'}$ are each hydrogen at positions 3, 4 or 6 of the pyrone ring; or a pharmaceutically acceptable salt or stereoisomer thereof.

Also as used herein, reference to "a" compound, salt, stereoisomer, or racemic mixture of formula (I) is intended to encompass "one or more" such compounds, salts or stereoisomers. Furthermore, reference to a "compound" of formula (I), as in the discussion below of pharmaceutical formulations, is also intended to include a salt, stereoisomer, or racemic mixture of the compound.

In a preferred embodiment, X is $-(CH_2)_n-$, wherein n is any of 0-6 and preferably any of 1-6, Y is >NH or >0 and Z is >CO.

Without prejudice to the generality of the compounds of the present invention, in a preferred embodiment of the compounds defined by formula (I), X is $-(CH_2)_2-$, Y is >NH or >O, Z is >C=O, Ar is an indole containing a bond, $R_3$ to X at position 3 of the indole ring, $R_1$ is methoxy on position 5 of the indole ring, each of $R_2$ and $R_4$ is hydrogen, Ar' is a gamma-pyrone bonded to Z at position 2 of the pyrone ring, $R_{1'}$ is hydrogen or a hydroxy group at position 5 of the pyrone ring and $R_{2'}$ is hydrogen or a carboxy group at position 6 of the gamma pyrone ring; or a pharmaceutically acceptable salt, stereoisomer, or racemic mixture thereof. In a second preferred embodiment, Ar is as defined above and Ar' is an alpha-pyrone ring bonded to Z at position 5 of the alpha-pyrone ring and $R_{1'}$ and $R_{2'}$ are hydrogens; or a pharmaceutically acceptable salt, stereoisomer, or racemic mixture thereof. Some exemplary compounds include e.g., N-[2-(1H-indol-3-yl)-ethyl]-comanilamide, N-[2-(5-methoxy-indol-3-yl)-ethyl]-comanilamide, and 2-methyl-4-oxo-4H-pyran-3-yl [2-(5-methoxy-1H-indol-3-yl)ethyl]carbamate.

Suitable pharmaceutically acceptable salts of the compounds of formula (I) include salts which may, for example, be formed by mixing a solution of the compound with a solution of a pharmaceutically acceptable acid. Pharmaceutically acceptable acids include, but are not limited to hydrochloric acid, fumaric acid, maleic acid, succinic acid, acetic acid, citric acid, benzoic acid, tartaric acid, carbonic acid, phosphoric acid or sulfuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also includes salts thereof, preferably non-toxic pharmaceutically acceptable salts thereof, such as the sodium, potassium and calcium salts thereof. Representative pharmaceutically acceptable salts include, yet are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

In some embodiments, the functional groups of the compounds of formula (I) useful in the invention can be modified to enhance the pharmacological utility of the compounds. Such modifications are well within the knowledge of a person of ordinary skill in the art and include, without limitation, esters, amides, ethers, N-oxides, and pro-drugs of the indicated compound of formula (I). Examples of modifications that can enhance the activity of the compounds of formula (I) include, for example, esterification such as the formation of $C_1$ to $C_6$ alkyl esters, preferably $C_1$ to $C_4$ alkyl esters, wherein the alkyl group is a straight or branched chain. Other acceptable esters include, for example, $C_1$ to $C_7$ cycloalkyl esters and arylalkyl esters such as benzyl esters. Such esters can be prepared from the compounds described herein using conventional methods well known in the art of organic chemistry.

It is understood that, in embodiments where the compounds of formula (I) useful in the invention have at least one chiral center, the compounds can exist as chemically distinct enantiomers. In addition, where a compound has two or more chiral centers, the compound can exist as diastereomers. All such isomers and mixtures thereof are encompassed within the scope of the indicated compounds of formula (I). Similarly, where the compounds possess a structural arrangement that permits the structure to exist as tautomers, such tautomers are encompassed within the scope of the indicated compound. Furthermore, in crystalline form, the compounds may exist as polymorphs; in the presence of a solvent, a compound may form a solvate, for example, with water or a common organic solvent. Such polymorphs, hydrates and other solvates also are encompassed within the scope of the invention as defined herein.

The present invention also includes in its scope pharmaceutical compositions containing as an active substance a therapeutically effective amount of a compound of formula (I), or a pharmaceutically acceptable salt thereof as well as any stereoisomer, covered by formula (I), in association with one or more pharmaceutically acceptable diluents, preservatives, solubilizers, emulsifiers, adjuvants, excipients or carriers conventionally used in pharmaceutical and veterinary formulations. The present pharmaceutical formulation can be adopted for administration to humans and/or animals.

The dosage of active agent in compositions of this disclosure can vary, provided that a therapeutic amount is administered. Such therapeutic amount generally is the minimum dose necessary to achieve the desired therapeutic effect, which can be, for example, that amount roughly necessary to reduce the dementia symptoms, e.g., enhance episodic memory. Desirably the active agent is administered to a patient (human or animal) in need of such treatment in dosages that will provide optimal pharmaceutical efficacy.

The selected dosage depends upon the nature and severity of the disease or disorder to be treated, desired therapeutic effect, the route of administration, and the duration of treatment. The dose will vary from patient to patient depending on the nature and severity of the disease, the patient's weight, special diets then being followed by the patient, concurrent medication, the bioavailability of the compound upon administration and other factors which those skilled in the art will recognize. Therapeutic doses are generally in the range of 0.1-1000 mg/day and can be, for example, in the range of 0.1-500 mg/day, 0.5-500 mg/day, 0.5-100 mg/day, 0.5-50 mg/day, 0.5-20 mg/day, 0.5-10 mg/day or 0.5-5 mg/day, with the actual amount to be administered determined by a physician taking into account the relevant circumstances including the severity of the dementia, the age and weight of the patient, the patient's general physical condition, the cause of dementia and the route of administration. In some embodiments, the therapeutically effective amount comprises a dosage of 0.10 mg, 0.15 mg, 0.20 mg, 0.25 mg, 0.5 mg, 0.75 mg, 1 mg, 2 mg, 2.5 mg, 3 mg, 4 mg, 5 mg, 6 mg, 7 mg, 8 mg, 9 mg, 10 mg, 15 mg, 20 mg, 25 mg, or 30 mg or 40 mg or 50 mg one or more times a day. As a non-limiting example, the compounds of the present invention may be administered by repeated dosing or continuous dosing over a period of at least three days, or for example, over three days, four days, five days, six days, seven days, eight days, nine days or ten days or chronically. As a further example, the compounds can be administered multiple times a day, such as twice per day, three times per day, four times per day or more.

A pharmaceutical composition useful in the invention includes the active compound (i.e. a compound of formula (I)) and further can include, if desired, an excipient such as a pharmaceutically acceptable carrier or a diluent, which is any carrier or diluent that has substantially no long term or permanent detrimental effect when administered to a subject. Such an excipient generally is mixed with active compound or permitted to dilute or enclose the active compound. A carrier can be a solid, semi-solid, or liquid agent that acts as an excipient or vehicle for the active compound. Examples of pharmaceutically acceptable carriers and diluents include, without limitation, water, such as distilled or deionized water; saline; and other aqueous media. It is understood that the active ingredients can be soluble or can be delivered as a suspension in the desired carrier or diluent.

The term "SNP" or "Single Nucleotide Polymorphism" has its general meaning in the art and refers to a single nucleotide variation in a genetic sequence that occurs at appreciable frequency in the population. The single nucleotide variation can be a substitution but also an addition or a deletion. There are millions of SNPs in the human genome. Most commonly, these variations are found in the DNA segments between genes.

According to the present invention, the term "genotype" means the 5' to 3' nucleotide sequence found at a set of one or more polymorphic sites in a locus on a single or on both chromosomes from a single individual.

According to the invention, the term "biological sample" refers to any sample isolated from a patient which permits DNA extraction. It can include, by way of example and not limitation, bodily fluids and/or tissue extracts such as homogenates or solubilized tissue obtained from a patient. Tissue extracts are obtained routinely from tissue biopsy and autopsy material or oral/nasal mucosa. Bodily fluids useful in the present invention include blood, urine, saliva or any other bodily secretion or derivative thereof.

As used herein "blood" includes whole blood, isolated mononuclear cells/lymphocytes (T cells, B cells, Natural Killer cells and monocytes, each having a nucleus), plasma, serum, circulating epithelial cells, constituents, or any derivative of blood. In a preferred embodiment of the invention, the sample to be tested is blood.

The term "responsiveness of a patient", "responder patient" or "responsive patient" refers to a patient who shows a desired response in a disease (e.g., relief of symptoms or improvement in intellectual ability in Schizophrenia) with treatment. The disease severity can be measured according to common general knowledge (CGK) standards in the art.

Single nucleotide polymorphisms in chromosome 2, 2:107,510,000-107,540,000 locus (as disclosed in the Genome Reference Consortium Human genome build 37 (GRCh37)) according to the invention, refers 1-6 single nucleotide polymorphism in chromosome 2; rs12328439 (2:107516926) and/or rs62155556 (2:107521253) and/or rs62155557 (2:107522069) and/or rs62155558 (2:107523546) and/or rs17033479 (2:107525598) and/or rs9789618 (2:107535946).

An aspect of the present disclosure relates to an in-vitro method for identification of a genomic loci predicting the responsiveness of a patient afflicted with a mental disorder (e.g., ASD, schizophrenia, or attention deficit disorders) to a pharmaceutical treatment, said method comprising the step of determining in a biological sample obtained from said patient the genotypes of a single nucleotide polymorphism (SNP) in chromosome 2, 2:107,510,000-107,540,000 locus.

In some aspects, the genotype of a patient is determined on a nucleic acid sample obtained from a biological sample from said patient. The nucleic acid sample may be obtained from any cell source or tissue biopsy. Non-limiting examples of cell sources available include without limitation blood cells, buccal cells, epithelial cells or fibroblasts. Cells may also be obtained from body fluids, such as blood or lymph, etc. DNA may be extracted using any methods known in the art, such as described by Dilhari et al., AMB Express volume 7, 179, (2017).

The SNPs may be detected in the nucleic acid sample, preferably after amplification. For instance, the isolated DNA may be subjected to amplification by polymerase chain reaction (PCR), using oligonucleotide primers that are specific for one defined genotype or that enable amplification of a region containing the polymorphism of interest. According to a first alternative, conditions for primer annealing may be chosen to ensure specific reverse transcription (where appropriate) and amplification; so that the appearance of an amplification product be a diagnostic of the presence of a particular genotype. In one aspect, DNA may be amplified, after which the genotype is determined in the amplified sequence by hybridization with a suitable probe or by direct sequencing, or any other appropriate method known in the art.

In some aspects, wherein said detecting step is performed using allele-specific probe hybridization, allele-specific primer extension, allele-specific amplification, sequencing, 5' nuclease digestion, molecular beacon assay, oligonucleotide ligation assay (OLA), size analysis, single-stranded conformation polymorphism analysis (SSCP), or denaturing gradient gel electrophoresis (DGGE).

In some aspects, the present disclosure includes use of an amplified polynucleotide containing the SNP at the positions defined herein, wherein an amplified polynucleotide is between about 16 and about 1,000 nucleotides in length, e.g., 20-100 nucleotides in length.

In some aspects, the present disclosure includes use of an isolated polynucleotide which specifically hybridizes to a nucleic acid molecule containing the single SNP at the positions defined herein, or a complement thereof.

In some aspects, the isolated polynucleotide is an allele-specific probe, an allele-specific primer.

In some aspects, the present disclosure includes a kit including a polynucleotide as defined herein, a buffer, and an enzyme, e.g., a DNA polymerase.

In some aspects, the present disclosure includes an allele-specific probe and the enzyme is a ligase, and the 3' end of the allele-specific probe aligns with the SNP and wherein the kit further comprises a second probe, which hybridizes to an adjacent segment of the nucleic acid molecule directly 3' to the allele-specific probe.

In some aspects, the SNPs may be identified by using suitable DNA chip technologies. Non-limiting examples include those described in documents EP1065280A2 and WO2002101094A1, which are incorporated herein by reference in their entireties.

In one aspect, if the human subject has been diagnosed with dementia with schizophrenia, an attention deficit disorder, or an autism spectrum disorder and has a single nucleotide polymorphism (SNP) in the 2:107,510,000-107,540,000 locus, the method includes administering a melatonin/5-HT1A receptor agonist to the human subject.

In one aspect, the present disclosure includes a method of identifying a genotype of a human subject afflicted with a neurological disorder or disease and then treating the human subject with a suitable treatment by determining if the human subject has a single nucleotide polymorphism (SNP) in the 2:107,510,000-107,540,000 locus and administering a melatonin/5-HT1A receptor agonist to the human subject if the human subject has been diagnosed with schizophrenia, an attention deficit disorder or an autism spectrum disorder and has a SNP in the 2:107,510,000-107,540,000 locus.

In one aspect, if the human subject has been diagnosed with schizophrenia, an attention deficit disorder or an autism spectrum disorder and does not have a SNP in the 2:107,510,000-107,540,000 locus, then the method further includes administering a medicament for treating schizophrenia, an attention deficit disorder or autism spectrum disorder that is not a melatonin/5-HT 1A receptor agonist to the subject.

In one aspect, the determining step is performed in-vitro using a nucleic acid-containing sample obtained from the subject.

In one aspect, the SNP is selected from 2:107516926 and/or 2:107521253 and/or 2:107522069 and/or 2:107523546 and/or 2:107525598 and/or 2:107535946, and/or a SNP in linkage disequilibrium with any one of said SNPs as disclosed in the Genome Reference Consortium Human genome build 37 (GRCh37), and wherein the human subject having the SNP has:

at least one C allele at rs12328439 (T>C); and/or
at least one A allele at rs62155556 (T>A); and/or
at least one T allele at rs62155557 (G>T); and/or
at least one A allele at rs62155558 (G>A); and/or
at least one G allele at rs17033479 (A>G); and/or
at least one A allele at rs9789618 (T>A).

In one aspect, the genotype of the subject at said positions of SNP is determined indirectly by determining the genotype of the subject at a position of SNP that is in linkage disequilibrium with said positions of SNP.

In one aspect, the determining step includes extracting and/or amplifying DNA from a sample obtained from the subject; and contacting the DNA with an array comprising a plurality of probes for determining the identity of at least one allele at a position of the defined SNPs.

In one aspect, the array is a DNA array, a DNA microarray or a bead array.

In one aspect, the administering step comprises administering a pharmaceutical composition comprising N-(2-(5-methoxy-1H-indol-3-yl)ethyl)-4-oxo-4H-pyran-2-carboxamide (piromelatine) and a pharmaceutically acceptable carrier.

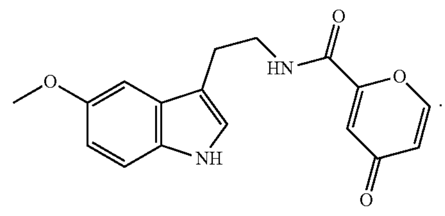

[piromelatine]

In one aspect, the pharmaceutical composition includes 1 to 100 mg piromelatine. In one aspect, 5 to 100 mg, 10, 15, 20, 25, 30, 35, 40, 45, 50, 55, 60, 65, 70, 75, 80, 85, 90, 95, or 100 mg piromelatine is administered to the subject daily. In one aspect, 20, 50, or 100 mg piromelatine is administered.

In one aspect, the method further includes administering the pharmaceutical composition in a combination therapy with an additional therapeutic agent for schizophrenia if the human subject has been diagnosed with schizophrenia, or with an additional therapeutic agent for autism spectrum disorder if the human subject has been diagnosed with an autism spectrum disorder, or with an additional therapeutic agent for attention deficit disorder if the human subject has been diagnosed with an attention deficit disorder. In some aspects, the human subject may be treated with, for example Aripiprazole (Abilify®), Asenapine (Saphris®), Brexpiprazole (Rexulti®), Cariprazine (Vraylar®), Clozapine (Clozaril®, Versacloz®), Iloperidone (Fanapt®), Lurasidone (Latuda®), Olanzapine (Zyprexa®), Paliperidone (Invega®), Quetiapine (Seroquel®), Risperidone (Risperdal®), Ziprasidone (Geodon®), Chlorpromazine, Fluphenazine, Haloperidol, Perphenazine, Thioridazine (Mellaril®), Thiothixene (Navane®), Trifluoperazine (Stelazine®), or other therapeutic agent for treating schizophrenia. In some aspects, the human subject may be treated with, for example, Risperidone (Risperdal®), Aripiprazole (Abilify®), or other therapeutic agent for treating ASD. In some aspects, the human subject may be treated with, for example, Adderall®, Dexedrine, Dextrostat®, Focalin®, Methylin®, Ritalin®, Metadate® CO, Ritalin® LA, Dexedrine Spansule, Vyvanse®, Concerta®, Daytrana®, Focalin® XR, Quillivant® XR, Intuniv®, Kapvay®, Strattera®, or other therapeutic agent for treating attention deficit disorder.

In one aspect, the present disclosure includes treating a patient diagnosed with schizophrenia, attention deficit or autism spectrum disorder and having a SNP selected from rs12328439 and/or rs62155556 and/or rs62155557 and/or rs62155558 and/or rs17033479 and/or rs9789618, comprising administering piromelatine to the patient.

In one aspect, the present disclosure includes predicting the response of a subject to a therapy comprising a melatonin/5-HT1A receptor agonist, by determining if the subject has a SNP selected from rs12328439 and/or rs62155556 and/or rs62155557 and/or rs62155558 and/or rs17033479 and/or rs9789618, wherein if the patient has been diagnosed with schizophrenia, an attention deficit disorder or an autism spectrum disorder, and has a SNP selected from rs12328439 and/or rs62155556 and/or rs62155557 and/or rs62155558 and/or rs17033479 and/or rs9789618 predicts that the subject will respond positively to a therapy comprising the melatonin/5-HT1A receptor agonist.

In one aspect, the method includes obtaining a nucleic acid-containing sample from the subject and contacting the nucleic acid with an array comprising a plurality of probes suitable for determining the identity of at least one allele at a position of the SNPs.

In one aspect, the present disclosure includes improving attention and focus a subject with an attention disorder associated with schizophrenia, an attention deficit disorder, or an autism spectrum disorder, comprising determining if the subject has a SNP in at least one of rs12328439 and/or rs62155556 and/or rs62155557 and/or rs62155558 and/or rs17033479 and/or rs9789618, and if the patient has the SNP, and if the subject has the SNP, then administering a melatonin/5-HT1A receptor agonist therapy to the subject.

In one aspect, the present disclosure includes identifying a prognostic genotype of a subject's response to a drug for treating mental disorders and/or intellectual ability in a human subject, the method comprising determining the genotype of the subject of at least 1 position of single nucleotide polymorphism (SNP) selected from 2:107516926 and/or 2:107521253 and/or 2:107522069 and/or 2:107523546 and/or 2:107525598 and/or 2:107535946, and/or a SNP in linkage disequilibrium with any one of said SNPs, wherein said SNPs are as disclosed in the GRCh37, and wherein the presence of:

at least one C allele at rs12328439 (T>C); and/or
at least one A allele at rs62155556 (T>A); and/or
at least one T allele at rs62155557 (G>T); and/or
at least one A allele at rs62155558 (G>A); and/or
at least one G allele at rs17033479 (A>G); and/or
at least one A allele at rs9789618 (T>A)
is indicative of a subject having a positive response to a melatonin/5-HT1A receptor agonist when the subject has been diagnosed with schizophrenia, an attention disorder, or an autism spectrum disorder, In one aspect, the determining step is performed in vitro using a nucleic acid-containing sample obtained from the subject.

In one aspect, the genotype of the subject at said positions of SNP is determined indirectly by determining the genotype of the subject at a position of SNP that is in linkage disequilibrium with said positions of SNP.

In one aspect, determining the genotype of the subject at said positions of SNP includes (i) extracting and/or amplifying DNA from a sample that has been obtained from the subject; and (ii) contacting the DNA with an array comprising a plurality of probes suitable for determining the identity of at least one allele at the SNP positions.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1—Piromelatine Tablets Preparation (10,000 Tablets Per Batch)

All ingredients were first sieved on a 30-mesh sieve. Starch 1500 (binder and disintegrant, 375 grams) and piromelatine (200 grams) were mixed in the V-blender for 5 minutes. Microcrystalline cellulose (filler/compression aid, 1550 grams) was added to the previously combined mixture and mixed in the V-blender for another 5 minutes to complete the internal phase. Microcrystalline cellulose (300 grams), Colloidal Silicon Dioxide (glidant, 37.5 grams) and magnesium stearate (lubricant, 37.5 grams) were combined separately in a V-blender as the external phase and blended for 2 minutes. The two mixtures were then combined and mixed in the blender for 1 minute. The blend was compressed using a 6 stations rotary tablet press machine with 8.0×16.0 mm (2.0 mm deep) oval concave die and punches.

Example 2 Performance of 2:107,510,000-107,540,000 Locus Polymorphism Carriers in the Computerized Neuropsychological Test Battery (cNTB)

The Computerized Neuropsychological Test Battery (CNTB), a new assessment tool for neuropsychopharmacologic research, is based on a neuropsychological approach. While it is based on tests previously shown to be sensitive to subtle changes in neuropsychological functioning, it differs from currently available tools for measuring central nervous system effects of new compounds (Veroff A E et al., A new assessment tool for neuropsychopharmacologic research: the Computerized Neuropsychological Test Battery. J Geriatr Psychiatry Neurol. 1991 October-December; 4(4):211-7.).

In a randomized, placebo controlled study of piromelatine (5, 20, and 50 mg daily for 6 months) in patients with early symptomatic Alzheimer's disease (n=352 age 60-85 years) no statistically significant differences between the drug and placebo treatment were observed in the intellectual ability measured by the global composite score of the computerized Neuropsychological Test Battery (cNTB), and the Alzheimer's Disease Assessment Scale cognitive subscale (ADAS-Cog14, considered the gold standard for assessing the efficacy of anti-dementia treatments). However, it was surprisingly found that patients had paradoxical responses to the drug in that cNTB improved significantly, whereas the ADAS-Cog14 deteriorated.

DNA extraction and SNP genotyping were performed as follows: For 107 patients, whole blood was collected at the time of enrollment, and genomic DNA was extracted from peripheral lymphocytes using a commercial kit. Variant genotyping of a combined Whole Genome and Whole Exome sequencing, was performed. The detection of variants associated with the response of the treatment was performed through a genome wide association study (GWAS) analysis (which is a known case-control paradigm). The setup involves taking the patients that respond to the treatment as case and the patients that do not respond to the treatment as controls. The general case-control allelic test was performed through a Cochran-Armitage trend test. These results were cross-checked against potential confounding variables, given as a stratification test. The stratification was assessed by a complete-linkage hierarchical clustering using the pairwise population concordance as a constraint. The SNP calling was done on the aligned BAM files using DRAGEN: support.illumina.com/help/DRAGEN_Germline_OLH_1000000083701/Content/Source/Informatics/Apps/DRAGENGermlineSmallVarCaller_appDRAG.htm and filter SNPs using VQSR: gatk.broadinstitute.org/hc/en-us/articles/360035531612-Variant-Quality-Score-Recalibration-VQSR. The SNP caller program takes mapped and aligned DNA reads as input and calls SNPs and indels through a combination of column-wise detection and local de novo assembly of haplotypes. Callable reference regions are first identified with sufficient alignment coverage. Within these reference regions, a fast scan of the sorted reads identifies active regions, centered around pileup columns with evidence of a variant. The active regions are padded with enough context to cover significant, nonreference content nearby and padded even more where there is evidence of indels.

Results

In a GWAS of a representative sample (N=107) of the study cohort identified a certain subpopulation (27% of the sample) with 1 to 6 single nucleotide polymorphism in chromosome 2, 2:107,510,000-107,540,000 locus in whom the piromelatine treatment resulted in a significant enhancement compared to baseline and significant enhancement over placebo in the change from baseline in cNTB. Surprisingly, there was a significant improvement in the ADAS-Cog14 scores following placebo treatment in the patients who were carriers of the 2:107,510,000-107,540,000 locus polymorphism (27% of the sample) on placebo treatment, indicative of alleviating the dementia in these patients (Table 1). No such effects were seen in the patients who were non-carriers of the 2:107,510,000-107,540,000 locus polymorphism (73% of the sample) who continues to deteriorate under placebo but not under piromelatine treatment supporting the different disease characteristics of these subgroups. (Table 1).

In a separate analysis, detection of the 6 single nucleotide polymorphisms in chromosome 2; rs12328439 (T>C), rs62155556 (T>A), rs62155557 (G>T), rs62155558 (G>A), rs17033479 (A>G) and rs9789618 (T>A), was performed on 11 extracted genomic DNA samples using the Bi-directional Sanger sequencing method by a different bioanalytical lab under blinded assessment. The 11 samples were of 5 carriers of the above 6 SNPs, 5 samples of non-carriers and one sample of a carrier of only 5 SNPs (missing the rs62155558 (G>A) SNP) representing the full group of 107 samples analyzed by the GWAS method. The results of the retesting fully confirmed the presence or absence of the 6 SNPs as determined using the GWAS method.

TABLE 1

Effects of piromelatine (5, 20 and 50 mg or Placebo daily for 26 weeks) on Alzheimer's Disease Assessment Scale-cognitive subscale (ADAS-Cog14) and cNTB scores in patients with symptomatic Alzheimer's disease who are carriers and non-carriers of 2:107,510,000-107,540,000 locus polymorphism.

| Variable | cNTB (5, 20 and 50 mg, N = 19) | cNTB (Placebo, N = 10) | ADAS-Cog14 (5, 20 and 50 mg, N = 19) | ADAS-Cog14 (Placebo, N = 10) |
|---|---|---|---|---|
| 2:107,510,000-107,540,000 locus polymorphism carriers | 0.38* | 0.04 | 0.63* | −3.10 |
| Improvement vs baseline | yes | ns | deter | yes |
| **Variable** | **cNTB (5, 20 and 50 mg, N = 59)** | **cNTB (Placebo, N = 19)** | **ADAS-Cog14 (5, 20 and 50 mg, N = 59)** | **ADAS-Cog14 (Placebo, N = 19)** |
| 2:107,510,000-107,540,000 locus polymorphism non-carriers | −0.04 | −0.09 | −1.07* | 1.65 |
| Improvement | ns | ns | yes | deter |

TABLE 1-continued

*significant compared to placebo, ns = non-significant effect, deter = deterioration compared to placebo.

The main performance domains in the cNTB that improved upon treatment of carriers of a 2:107,510,000-107,540,000 locus polymorphism with the 20 mg piromelatine dose were the episodic memory domain composite score and attention domain composite score. The main domains that deteriorated in the ADAS-Cog14 test were in difficulty engaging in successful problem-solving thought and action which are known difficulties in schizophrenia (Morris et al Schizophrenia Research 1995; 14 (Issue 3): 235-246). In addition, mean sleep quality index (PSQI) did not improve in 2:107,510,000-107,540,000 locus polymorphism carriers, but improved in non-carriers whereas neuropsychiatric inventory (NPI) improved in 2:107,510,000-107,540,000 locus polymorphism carriers and less so in non-carriers (Table 2). The improvement in NPI in the 2:107,510,000-107,5430,000 locus polymorphism carriers was mainly due to improvement in aberrant movements, which are also quite prevalent in schizophrenia (Schappi et al. Distinct Associations of Motor Domains in Relatives of Schizophrenia Patients-Different Pathways to Motor Abnormalities in Schizophrenia?. Front Psychiatry. 2018; 9:129).

Surprisingly, the deterioration in ADAS-Cog14 in the 2:107,510,000-107,540,000 locus polymorphism carriers was negatively correlated with improvement in NPI (Table 2). On the other hand, the change in ADAS-Cog14 in the 2:107,510,000-107,540,000 locus polymorphism carriers was significantly correlated with the change in PSQI (both deteriorate) linking the deterioration in ADAS-Cog14 with a paradoxical response to the sleep promoting effects of piromelatine leading to lack of sleep (Table 2). This association was not present at lower doses (5 mg) of piromelatine which led to improvement in cNTB without worsening of ADAS-Cog or sleep quality (Table 3).

These findings suggest that the benefits produced by piromelatine in the carriers of the 2:107,510,000-107,540,000 locus polymorphism were more marked within the domain of intellectual ability, specifically alertness, and within the aberrant motor activity domain, all of which are beneficial to patients with schizophrenia, ASD, and attention deficit disorders because of the paradoxical response in those patients to effects of melatonin/5-HT1A agonists.

TABLE 2

Effects of piromelatine (20 mg daily for 26 weeks) on symptomatic Alzheimer's Disease Assessment Scale-cognitive subscale (ADAS-Cog14) and cNTB scores in patients with mild dementia due to symptomatic Alzheimer's disease who carry 2:107,510,000-107,540,000 locus polymorphism (upper panel (n = 12) and who do not carry 2:107,510,000-107,540,000 locus polymorphism (n = 23).

| | | | | ADAS-Cog14 | | | |
|---|---|---|---|---|---|---|---|
| Variable | cNTB Change | NPI from baseline | PSQI | Change from baseline | Correlation with change in NPI | Correlation with change in PSQI | % Responders (decrease ≥ 4) |
| 2:107,510,000-107,540,000 locus polymorphism carriers (N = 12) | 0.44 | −3.08 | −0.17 | 3.58 | R = 0.73* | R = 0.57* | 8 |
| Improvement: | yes | yes | ns | deter | | | |
| 2:107,510,000-107,540,000 locus polymorphism non-carriers (N = 23) | −0.06 | −2.70 | −2.13 | −2.91 | R = 0.1 | R = 0.29 | 39 |
| Improvement: | ns | yes | yes | yes | | | |

*significant correlation, ns = non-significant effect, deter = deterioration.

Paradoxically, the deterioration in ADAS-Cog14 was significantly correlated with improvement in NPI (neuropsychiatric index) and deterioration in sleep quality.

The present disclosure includes the use of other melatonin/5-HT1A agonists that activate the same receptors to elicit similar responses. The binding data in Example 4 show that piromelatine is an agonist of both receptors.

Example 3—Low Dose Therapy of Symptomatic AD Patients that are Carriers of a 2:107,510,000-107,540,000 Locus Polymorphism The changes in cNTB, ADAS-Cog14 and PSQI for the low dose (5 mg) of piromelatine were analyzed (Table 3). In particular it can be seen that patients treated with (5 mg) piromelatine who carried the polymorphism did not deteriorate or tended to improve (Cohen's d>0.2) on the ADAS-Cog14 or PSQI (Table 3). However, only carriers of a 2:107,510,000-107,540,000 locus polymorphism improved on the cNTB upon treatment with the 5 mg piromelatine dose and the main performance domains being the episodic memory domain composite score and attention domain composite score. This finding suggests that patients with symptomatic Alzheimer disease who are carriers of a 2:107,510,000-107,540,000 locus polymorphism may improve on low dose piromelatine. They further demonstrate that the presence of 2:107,510,000-107,540,000 locus polymorphism represents a distinct type of dementia that differ from Alzheimer's disease.

TABLE 3

Effects of piromelatine (5 mg daily for 26 weeks) on symptomatic Alzheimer's Disease Assessment Scale-cognitive subscale (ADAS-Cog14) PSQI and cNTB scores in patients with mild dementia due to symptomatic Alzheimer's disease who carry 2:107,510,000-107,540,000 locus polymorphism (upper panel (n = 15) compared to patients who do not carry 2:107,510,000-107,540,000 locus polymorphism (n = 38). Cohen's d is defined as the difference between two means divided by a standard deviation for the data and d > 0.2 means a considerable effect size. (Sawilowsky, S (2009). "New effect size rules of thumb". Journal of Modern Applied Statistical Methods. 8 (2): 467-474).

| | Change from Baseline | | |
|---|---|---|---|
| Variable | cNTB | ADAS Cog14 | PSQI |
| 2:107,510,000-107,540,000 locus polymorphism carriers | | | |
| Placebo (N = 10) | 0.04 | −3.10 | −3.80 |
| Piromelatine 5 mg (N = 5) | 0.28 | −6.40 | −3.40 |
| Cohen's vs placebo >0.2 | improvement | improvement | no improvement |
| 2:107,510,000-107,540,000 locus polymorphism non-carriers | | | |
| Placebo (N = 19) | −0.09 | 1.65 | −0.06 |
| Piromelatine 5 mg (N = 19) | −0.21 | 1.11 | −1.11 |
| Cohen's d vs placebo >0.20 | deterioration | no improvement | improvement |

Based on these results in this patient population of symptomatic AD patients that are carriers of a 2:107,510,000-107,540,000 locus polymorphism, the present disclosure includes administration of piromelatine and other melatonin/5-HT1A agonists at up to half the clinically effective dose (a "low dose" composition) in symptomatic AD patients that do not have the 2:107,510,000-107,540,000 locus polymorphism, e.g., up to 10 mg, up to 8 mg, around 5 mg doses. The present disclosure includes administering other melatonin/5-HT1A agonists that activate the same receptors to elicit similar responses. The binding data in Example 4 show that piromelatine is an agonist of both receptors.

Example 4—Piromelatine Binding Assays

For receptor binding assays, stably expressing 5-HT1a, 1b, 1c and 2c receptors cells (HEK-293, rat cerebral cortex, CHO and HEK-293, respectively) were incubated with 0.3 or 1 nM of their respective radioligand ($^{3}$H—OH-DPAT, $^{125}$I CYP, $^{3}$H serotonin and $^{3}$H-mesulergine) alone or in the presence of 1 nM to 10 μM of piromelatine. The bound radioligand was assessed. Non-specific binding was evaluated under the reaction contained with 8-OH-PTA, serotonin and RS-10221 (8[-5-(2,4-Dimethoxy-5-(4-trifluoromethylphenylsulphonamido)phenyl-5-oxopentyl]-1,3,8-triazaspiro[4.5]decane-2,4-dione hydrochloride).

For the functional assay, Homogeneous Time Resolved Fluorescence (HTRF) was used to measure cAMP or IPI as products of the functional agonist or antagonist binding of 5-HT1a, 2a,2b, 2c, 4e, 6, 7 to their respective ligand (8-OG-DPAT or serotonin). Cellular dielectric spectroscopy was used to measure impedance as the product of the functional agonist or antagonist binding of 5HT1b and determine their respective ligand (serotonin).

A full profile of binding parameters to an additional 60 different ion channels and receptors of different neurotransmitters and hormones was performed (data not shown because none of the 60 receptor assays yielded a significant (>50%) inhibition by 10 μM of piromelatine).

Results

The results, shown in Table 4 demonstrate the competition of piromelatine on specific 5-HT receptors binding with a low affinity to 5-$HT_{1A}$, 5-$HT_{1B}$, 5-$HT_{2A}$, 5-$HT_{2C}$ and 5-$HT_{2B}$ receptors.

TABLE 4

Effects of piromelatine on binding to 5-HT receptor subtypes: binding parameters (IC50 is the concentration causing 50% inhibition of binding).

| Receptor's subtype | IC50 (μM) |
|---|---|
| 5-HT-1a | 0.6 |
| 5-HT-1b | 8 |
| 5-HT-1d | 0.46 |
| 5-HT-2a | >10 |
| 5-HT-2b | 6.78 |
| 5-HT-2c | 2.8 |
| 5-HT-4 | >10 |
| 5-HT-6 | >10 |
| 5-HT-7 | >10 |

In the functional assays, moderate agonist activity of piromelatine was detected for 5HT1a and 5-HT1d. Low agonist activity was detected for 5-HT1b.

The results show that these melatonin/5-HT1A, 1D agonists elicit responses like those of melatonin and serotonin in vitro. In addition, these assays show that at lower dose levels, the serotonergic activity will be less, so the ratio between melatoninergic and serotonergic activities can be modulated to obtain the desired treatment responses.

Example 5

Clinically diagnosed AD onset distributions were constructed from information on age at onset of AD (date of clinical AD diagnosis), presence/absence of APOE-4 allele and presence/absence of a 2:107,510,000-107,540,000 locus polymorphism in subjects of the study presented in Example 2. The % of subjects diagnosed clinically for AD at age<65 was compared between carriers and non-carriers on the 2:107,510,000-107,540,000 locus polymorphism groups separately for E4 carriers and non-carriers. The results indicated that the percentage of subjects diagnosed at age<65 years (early onset dementia) was almost double in carriers of a 2:107,510,000-107,540,000 locus polymorphism than non-carriers and this distinct diagnosis was augmented in those carrying at least 1 APOE-4 allele.

| APOE-4 | SNP | N < 65 | N total | % early onset (Under age of 65) | Pval % early onset |
|---|---|---|---|---|---|
| None | Non-SNPs | 8 | 37 | 22% | |
| None | SNPs | 7 | 17 | 41% | 0.0038* |
| E4 | Non-SNPs | 12 | 41 | 29% | |
| E4 | SNPs | 7 | 12 | 58% | 0.000035** |

Figure 4:
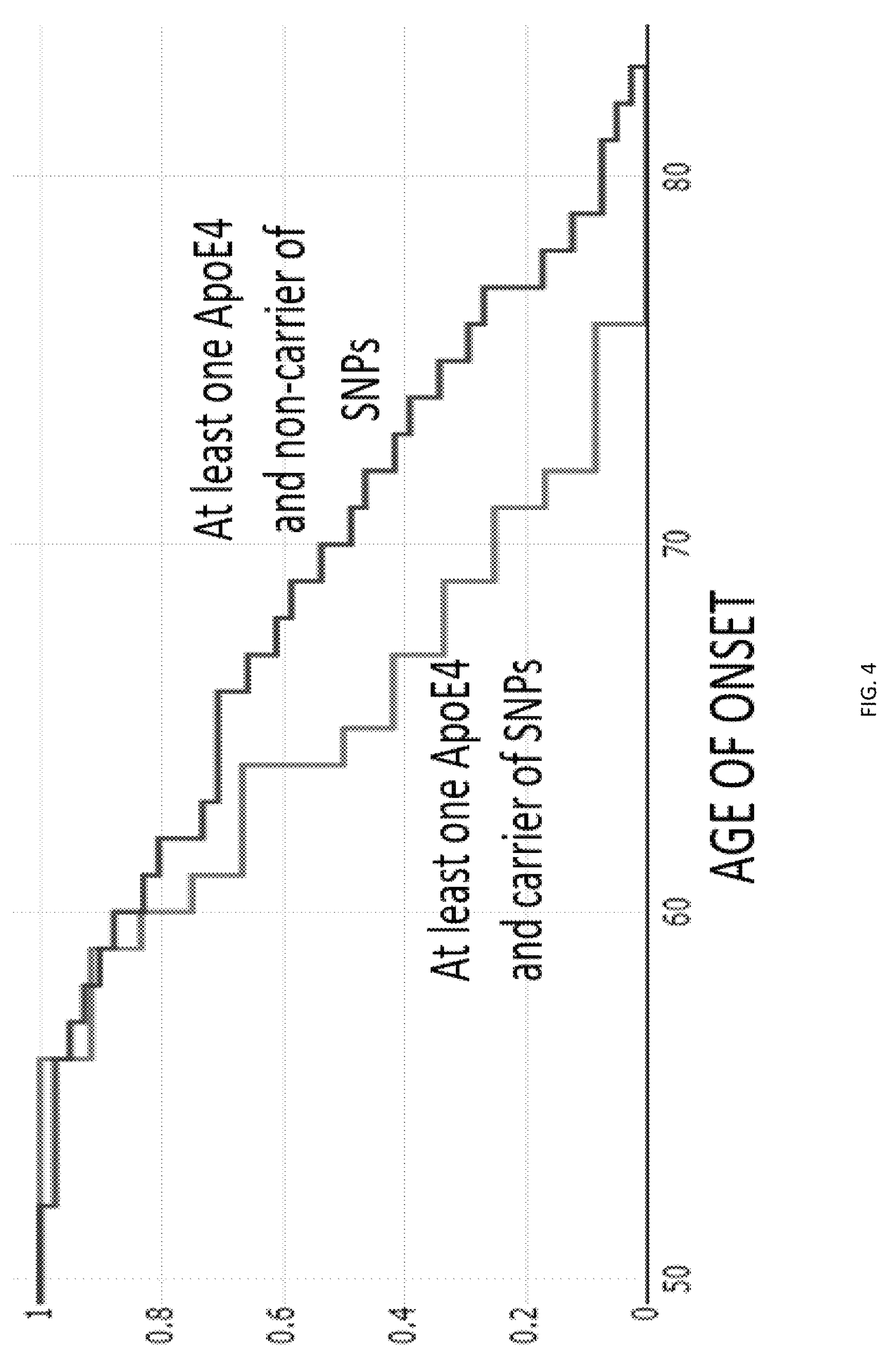
FIG. 4 shows the age at onset of AD distribution for subjects with at least 1 ApoE4 alleles in carriers (N=12; red line) and non-carriers (N=41; blue line) of the Single nucleotide polymorphism in chromosome 2, 2:107,510,000-107,540,000 locus. Onset curves, estimated by Kaplan-Meier product limit distributions, were clearly distinct (Chi square test statistic $x^2$=5.79, 1 degree of freedom, p<0.0160).
Figure 5:
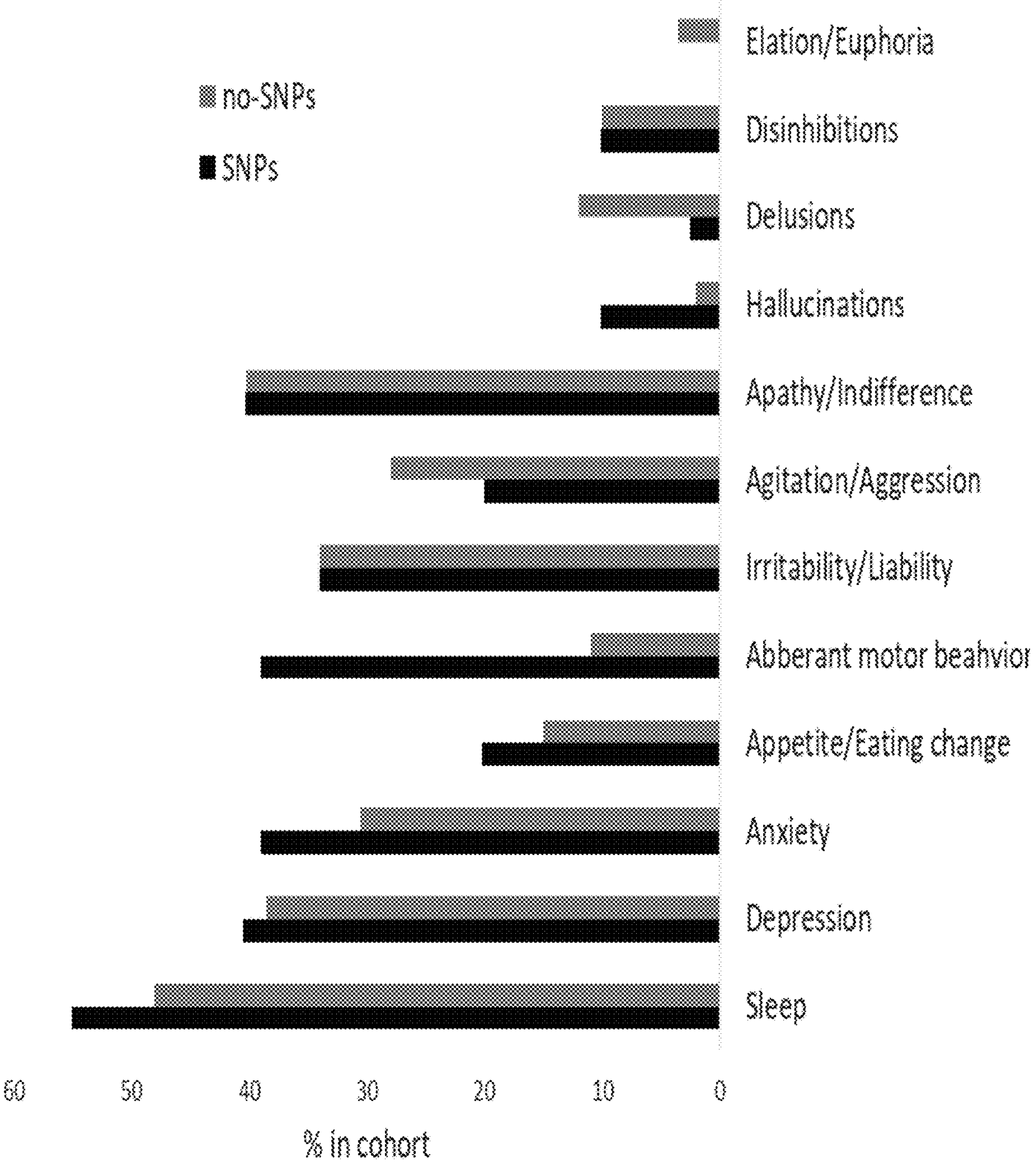
FIG. 5 shows neuropsychiatric symptoms (Neuropsychiatric Inventory; NPI, Cummings et al. Neurology, 1994; 44: 2308-2314.) in subpopulations of demented patients with clinically diagnosed Alzheimer's disease who are carriers and non-carriers of the Single nucleotide polymorphism in chromosome 2, 2:107,510,000-107,540,000 locus demonstrating a markedly four fold higher abundance of aberrant motor behavior in the carriers.

*Significant at p < 0.05, Chi-Square statistics
Significant at p < 0.01, Chi-Square statistics FIG. 4** shows the age at onset of AD distribution for subjects with at least 1 ApoE4 alleles in carriers (N=12; red line) and non-carriers (N=41; blue line) of a 2:107,510,000-107,540,000 locus polymorphism. Onset curves, estimated by Kaplan-Meier product limit distributions, were clearly distinct (Chi square test statistic $x^2$=5.79, 1 degree of freedom, p<0.0160). In the presence of at least 1 ApoE-4 allele, median AD onset age occurred 5.6 years earlier in 2:107,510,000-107,540,000 locus polymorphism carriers (64.6 years in carriers and 70.20 years in non-carriers). Because the presence of 1 allele of APOE-4 is not considered to advance AD disease onset (Blacker et al 1997), the present data demonstrate that 2:107,510,000-107,540,000 locus polymorphism is useful for diagnosis of early onset dementia and the method of the disclosure.

Example 6: Testing protocol for the Safety and efficacy of Piromelatine in participants with Mild Cognitive Impairment (MCI) and plausible Cognitive Impairment Associated With Schizophrenia (CIAS) or ASD Subjects with MCI and aberrant motor behavior symptoms or plausible CIAS are recruited. Whole genome sequencing is performed to detect whether they have chromosome 2q12, 2:107,510,000-107,540,000 locus polymorphism (6SNP). Those with polymorphism are entered into a randomized, double blind, parallel group, placebo controlled, multicenter study of Piromelatine 5 and 20 mg (40 subjects per group daily for 6 months).

The primary efficacy endpoint cNTB. Secondary endpoints are the Working Memory Domain of the MATRICS Consensus Cognitive Battery (MCCB) and the Neuropsychiatric Battery (NPI). An efficacy analysis is to be performed after 6 months double blind period.

Low dose therapy of piromelatine improves motoric skills, increases focus, and improves behavioral deficits in patients suffering from dementia, specifically dementia related to schizophrenia and dementia related to ASD or attention deficit disorder that are carriers of a 2:107,510,000-107,540,000 locus polymorphism. These changes are detected by a significant increase in the cTNB score and other cognitive performance tests.

Any of the above protocols or similar variants thereof can be described in various documentation associated with a pharmaceutical product. This documentation can include, without limitation, protocols, statistical analysis plans, investigator brochures, clinical guidelines, medication guides, risk evaluation and mediation programs, prescribing information and other documentation that may be associated with a pharmaceutical product. The present disclosure also includes embodiments wherein such documentation is physically packaged with a pharmaceutical product according to the present disclosure as a kit, as may be beneficial or as set forth by regulatory authorities.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations are not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A method of identifying and treating a human subject having dementia with schizophrenia, an attention deficit disorder, or an autism spectrum disorder comprising:

a) directly detecting that the human subject is a carrier of an allele of a single nucleotide polymorphism (SNP) comprising:
  at least one C allele at rs12328439 (T>C), and/or
  at least one A allele at rs62155556 (T>A), and/or
  at least one T allele at rs62155557 (G>T), and/or
  at least one A allele at rs62155558 (G>A), and/or
  at least one G allele at rs17033479 (A>G), and/or
  at least one A allele at rs9789618 (T>A); and b) administering a melatonin/5HT1A receptor agonist to the subject.

2. The method of claim 1, wherein the directly detecting step is performed in vitro using a nucleic acid-containing sample obtained from the human subject.

3. The method of claim 1, wherein the directly detecting step comprises:

extracting and/or amplifying DNA from a sample obtained from the subject; and contacting the DNA with an array comprising a plurality of probes for determining the identity of at least one allele at a position of SNP as follows:
  at least one C allele at rs12328439 (T>C); and/or
  at least one A allele at rs62155556 (T>A); and/or
  at least one T allele at rs62155557 (G>T); and/or
  at least one A allele at rs62155558 (G>A); and/or
  at least one G allele at rs17033479 (A>G); and/or
  at least one A allele at rs9789618 (T>A).

4. The method of claim 3, wherein the array is a DNA array, a DNA microarray or a bead array.

5. The method of claim 1, further comprising determining if the human subject is a carrier of an APOE4 gene.

6. The method of claim 1, wherein the administering step comprises administering a pharmaceutical composition comprising the melatonin/5HT1A receptor agonist and a pharmaceutically acceptable carrier.

7. The method of claim 6, wherein the pharmaceutical composition comprises 3 to 100 mg piromelatine.

8. The method of claim 6, comprising administering 20 mg piromelatine to the subject.

9. The method of claim 6, comprising administering piromelatine to the subject daily.

10. The method of claim 6, comprising administering 3-50 mg piromelatine to the subject daily.

11. A method of identifying a genotype of a human subject afflicted with dementia symptoms and then treating the human subject with a suitable treatment, the method comprising:

(i) directly detecting whether the human subject is a carrier of an allele of a single nucleotide polymorphism (SNP) comprising:
  at least one C allele at rs12328439 (T>C); and/or
  at least one A allele at rs62155556 (T>A); and/or
  at least one T allele at rs62155557 (G>T); and/or
  at least one A allele at rs62155558 (G>A); and/or at least one G allele at rs17033479 (A>G); and/or
at least one A allele at rs9789618 (T>A);
or directly detecting that the subject is not a carrier of:
at least one C allele at rs12328439 (T>C); and/or
at least one A allele at rs62155556 (T>A); and/or
at least one T allele at rs62155557 (G>T); and/or
at least one A allele at rs62155558 (G>A); and/or
at least one G allele at rs17033479 (A>G); and/or
at least one A allele at rs9789618 (T>A); and (ii) treating the human subject by:

a) administering a melatonin/5-HT1A receptor agonist to the human subject that has been diagnosed with schizophrenia, an attention deficit disorder, or an autism spectrum disorder and is a carrier; or b) administering a therapeutic agent that is not a melatonin/5-HT1A receptor agonist to the human subject that has been diagnosed with schizophrenia, an attention deficit disorder, or an autism spectrum disorder and is not a carrier.

12. The method of claim 11, wherein the detecting step is performed in vitro using a nucleic acid-containing sample obtained from the subject.

13. The method of claim 11, wherein the subject is a carrier and the treating step comprises administering 3 to 10 mg piromelatine per day.

14. The method of claim 11, wherein the detecting step comprises:

extracting and/or amplifying DNA from a sample obtained from the subject; and contacting the DNA with an array comprising a plurality of probes for detecting the identity of at least one allele at a position of the SNP.

15. The method of claim 14, wherein the array is a DNA array, a DNA microarray or a bead array.

16. The method of claim 11, wherein the administering step comprises administering a pharmaceutical composition comprising piromelatine and a pharmaceutically acceptable carrier.

17. The method of claim 11, wherein the pharmaceutical composition comprises 1 to 100 mg piromelatine.

18. The method of claim 17, comprising administering 1 to 100 mg piromelatine to the subject daily.

19. The method of claim 18, comprising administering 5-50 mg piromelatine to the subject daily.

20. The method of claim 11, further comprising administering an additional therapeutic agent for schizophrenia if the human subject has been diagnosed with schizophrenia, or with an additional therapeutic agent for an attention deficit disorder if the human subject has been diagnosed with an attention deficit disorder, or with an additional therapeutic agent for autism spectrum disorder if the human subject has been diagnosed with an autism spectrum disorder.

21. A method comprising administering a melatonin/5HT1A receptor agonist to a human subject diagnosed with dementia and carrying at least one C allele at rs12328439 (T>C); and/or
at least one A allele at rs62155556 (T>A); and/or
at least one T allele at rs62155557 (G>T); and/or
at least one A allele at rs62155558 (G>A); and/or
at least one G allele at rs17033479 (A>G); and/or
at least one A allele at rs9789618 (T>A).

* * * * *

SEQUENCE LISTING

```
Sequence total quantity: 12
SEQ ID NO: 1            moltype = DNA  length = 49
FEATURE                 Location/Qualifiers
source                  1..49
                        mol_type = other DNA
                        organism = Homo sapiens
SEQUENCE: 1
ttcttgctcc ccactaggtc acaatgtcct agcatcatca accctaaca              49

SEQ ID NO: 2            moltype = DNA  length = 49
FEATURE                 Location/Qualifiers
source                  1..49
                        mol_type = other DNA
                        organism = Homo sapiens
SEQUENCE: 2
ttcttgctcc ccactaggtc acaacgtcct agcatcatca accctaaca              49

SEQ ID NO: 3            moltype = DNA  length = 49
FEATURE                 Location/Qualifiers
source                  1..49
                        mol_type = other DNA
                        organism = Homo sapiens
SEQUENCE: 3
ccattcccct ttgagcctgg agattttaat tgaataaaaa ttacaaatt              49

SEQ ID NO: 4            moltype = DNA  length = 49
FEATURE                 Location/Qualifiers
source                  1..49
                        mol_type = other DNA
                        organism = Homo sapiens
SEQUENCE: 4
ccattcccct ttgagcctgg agatattaat tgaataaaaa ttacaaatt              49

SEQ ID NO: 5            moltype = DNA  length = 49
FEATURE                 Location/Qualifiers
source                  1..49
                        mol_type = other DNA
                        organism = Homo sapiens
SEQUENCE: 5
acgctttttt gaaataatga gagcgcactt caacagagaa ggctttgga              49

SEQ ID NO: 6            moltype = DNA  length = 49
FEATURE                 Location/Qualifiers
source                  1..49
                        mol_type = other DNA
                        organism = Homo sapiens
SEQUENCE: 6
acgctttttt gaaataatga gagctcactt caacagagaa ggctttgga              49

SEQ ID NO: 7            moltype = DNA  length = 49
FEATURE                 Location/Qualifiers
source                  1..49
                        mol_type = other DNA
                        organism = Homo sapiens
SEQUENCE: 7
```

-continued

```
ccttcctgag ccactgaagg ttgtggggaa aataatttaa cacttcagt            49

SEQ ID NO: 8            moltype = DNA  length = 49
FEATURE                 Location/Qualifiers
source                  1..49
                        mol_type = other DNA
                        organism = Homo sapiens
SEQUENCE: 8
ccttcctgag ccactgaagg ttgtagggaa aataatttaa cacttcagt            49

SEQ ID NO: 9            moltype = DNA  length = 49
FEATURE                 Location/Qualifiers
source                  1..49
                        mol_type = other DNA
                        organism = Homo sapiens
SEQUENCE: 9
ctgggttgcc cagggagctt gtctatacca gagtggctaa aattatgtc            49

SEQ ID NO: 10           moltype = DNA  length = 49
FEATURE                 Location/Qualifiers
source                  1..49
                        mol_type = other DNA
                        organism = Homo sapiens
SEQUENCE: 10
ctgggttgcc cagggagctt gtctgtacca gagtggctaa aattatgtc            49

SEQ ID NO: 11           moltype = DNA  length = 49
FEATURE                 Location/Qualifiers
source                  1..49
                        mol_type = other DNA
                        organism = Homo sapiens
SEQUENCE: 11
aaatgaggac actggatgat attgttaacc tttggtgatg ctaactaaa            49

SEQ ID NO: 12           moltype = DNA  length = 49
FEATURE                 Location/Qualifiers
source                  1..49
                        mol_type = other DNA
                        organism = Homo sapiens
SEQUENCE: 12
aaatgaggac actggatgat attgttaacc tttggtgatg ctaactaaa            49
```